United States Patent
Truong

(10) Patent No.: US 9,744,350 B2
(45) Date of Patent: Aug. 29, 2017

(54) METHOD FOR THE IMPLANTATION OF ACTIVE FIXATION MEDICAL LEADS

(71) Applicant: PACESETTER, INC., Sylmar, CA (US)

(72) Inventor: Frank Hieu Truong, El Monte, CA (US)

(73) Assignee: PACESETTER, INC., Sylmar, CA (US)

( * ) Notice: Subject to any disclaimer, the term of this patent is extended or adjusted under 35 U.S.C. 154(b) by 646 days.

(21) Appl. No.: 14/260,019

(22) Filed: Apr. 23, 2014

(65) Prior Publication Data

US 2014/0236171 A1    Aug. 21, 2014

Related U.S. Application Data

(62) Division of application No. 12/392,934, filed on Feb. 25, 2009, now Pat. No. 8,747,417.

(51) Int. Cl.
    *A61N 1/05*        (2006.01)
    *A61B 17/00*       (2006.01)

(52) U.S. Cl.
    CPC .. *A61N 1/0573* (2013.01); *A61B 2017/00243* (2013.01)

(58) Field of Classification Search
    CPC ................ A61N 1/0573; A61B 2017/00243
    See application file for complete search history.

(56) References Cited

U.S. PATENT DOCUMENTS

| 4,046,034 A * | 9/1977 | Flewelling .............. B25B 13/14 81/165 |
| 5,228,455 A | 7/1993 | Barcel |
| 2006/0253179 A1 | 11/2006 | Goode et al. |

FOREIGN PATENT DOCUMENTS

EP    1620164 B1    4/2007

OTHER PUBLICATIONS

Restriction Requirement, mailed Feb. 16, 2012—Parent U.S. Appl. No. 12/392,934.
NonFinal Office Action, mailed Feb. 12, 2013—Parent U.S. Appl. No. 12/392,934.
Final Office Action, mailed Dec. 16, 2013—Parent U.S. Appl. No. 12/392,934.
Notice of Allowance, mailed Apr. 11, 2014—Parent U.S. Appl. No. 12/392,934.

* cited by examiner

*Primary Examiner* — Katherine M Shi
*Assistant Examiner* — Michael Mendoza

(57) ABSTRACT

A lead implantation tool is used for the implantation of active fixation medical leads. The tool may be configured to operably couple to a lead connector end of an implantable cardiac electrotherapy lead including an active fixation helix tip and wherein the lead connector end includes a contact pin proximally extending from the lead connector end. The tool may include a feature configured to couple to the contact pin and a first mechanism configured to convert linear movement into rotational movement of the contact pin relative to the lead connector end. The tool may further include a second mechanism that causes a stylet extending through the tool and into the contact pin to at least one of distally and proximally displace within the contact pin.

5 Claims, 4 Drawing Sheets

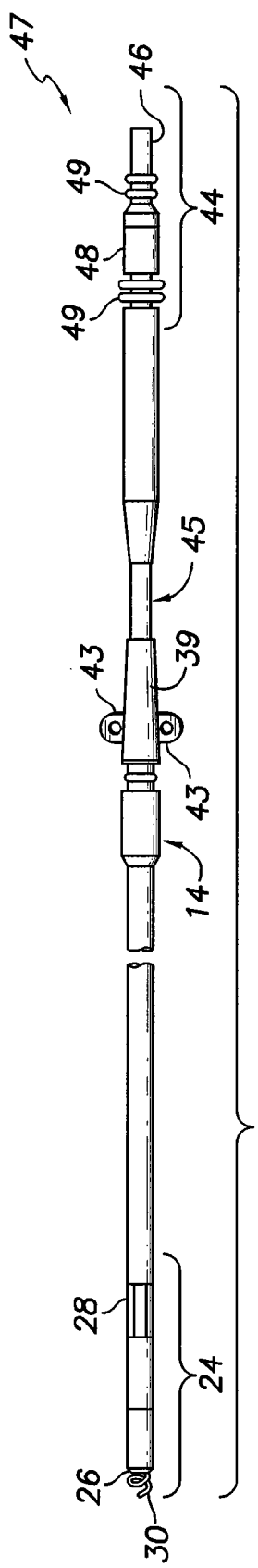
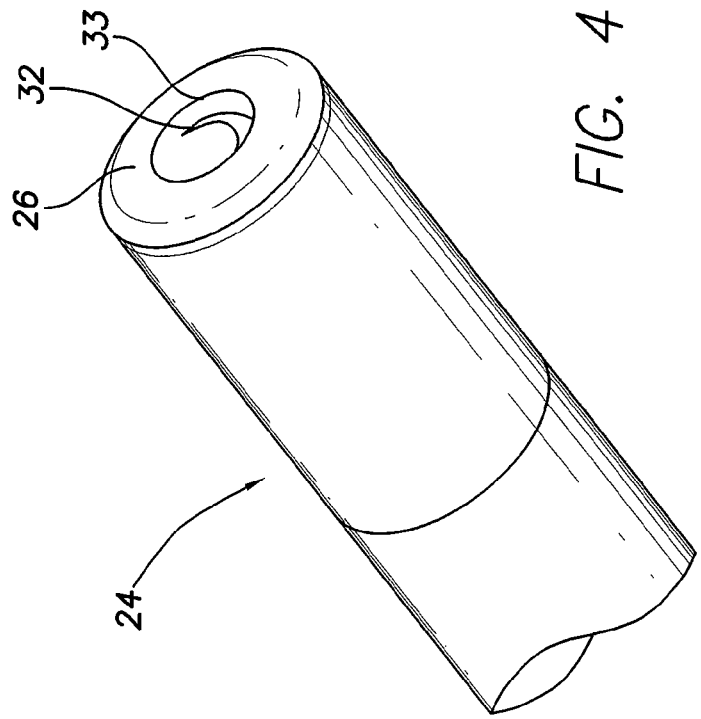

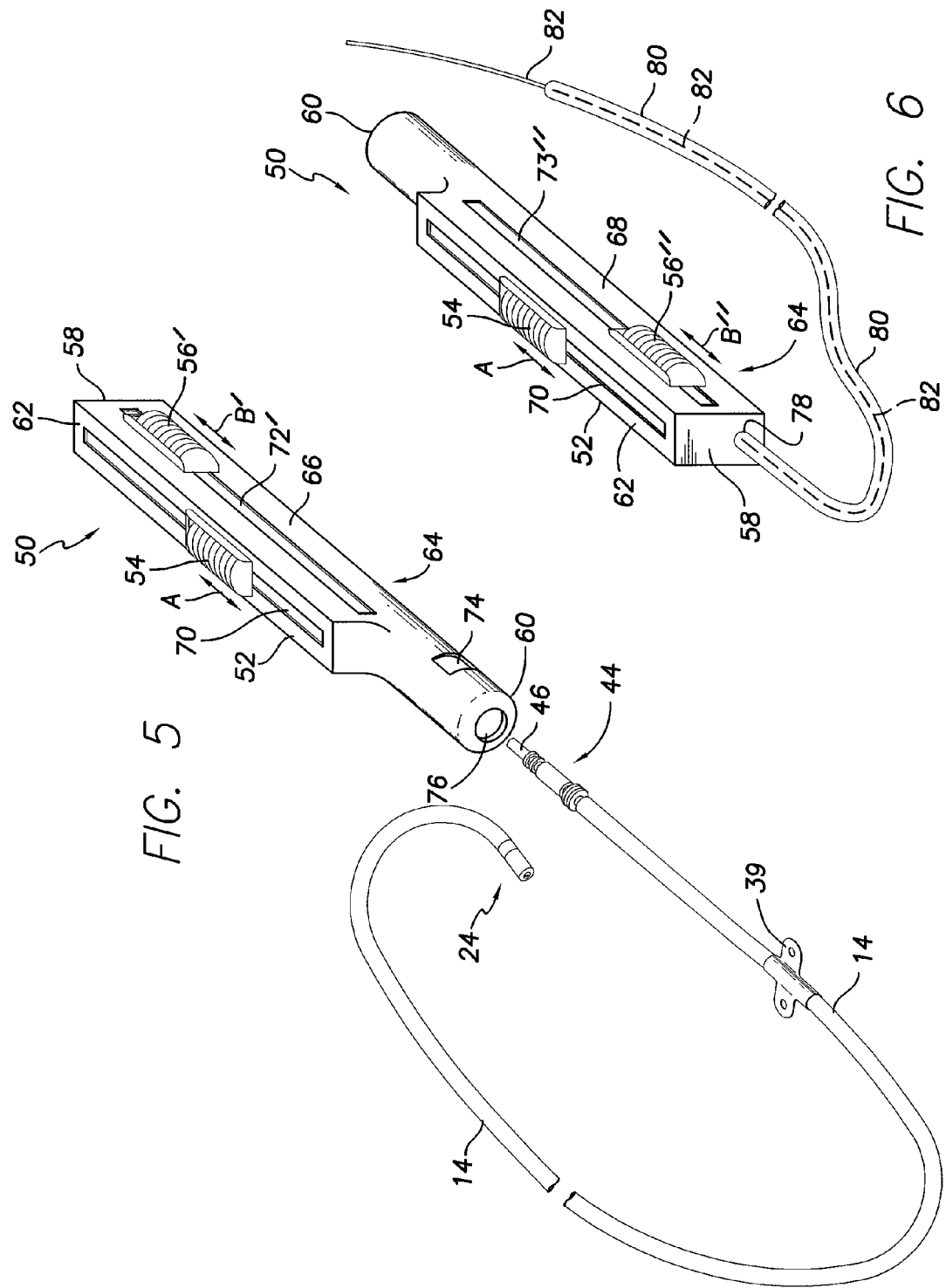

METHOD FOR THE IMPLANTATION OF ACTIVE FIXATION MEDICAL LEADS

CROSS REFERENCE TO RELATED APPLICATIONS

This application is a division of U.S. patent application Ser. No. 12/392,934, filed Feb. 25, 2009.

FIELD OF THE INVENTION

The present invention relates to medical apparatus and methods. More specifically, the present invention relates to tools and methods for the delivery and implantation of implantable medical leads.

BACKGROUND OF THE INVENTION

An active fixation lead may utilize a helix at its distal end for fixation into the heart tissue. The lead may have a lead connector end at its proximal end that includes a contact pin that is welded to an inner coil, which extends through the lead body and is welded to the helix at the distal end of the inner coil. The helix, inner coil and contact pin are rotatable as a unit within the lead body.

In order to extend the helix from the distal end of the lead body and anchor the helix into to heart tissue, a clip-on tool or implant tool is used to rotate the contact pin relative to rest of the lead connector end and the lead body. The effectiveness of this helix fixation method varies based on the number of contact pin rotations. For example, insufficient rotation can result in inadequate helix fixation to the heart tissue, and excessive rotation can damage the weld joints or result in perforation of the heart wall.

There is a need in the art for a lead delivery device that facilitates proper fixation of the helix to heart tissue. There is also a need in the art for a method of achieving proper fixation of the helix to heart tissue.

BRIEF SUMMARY OF THE INVENTION

A lead implantation tool is disclosed herein. In one embodiment, the tool is configured to operably couple to a lead connector end of an implantable cardiac electrotherapy lead including an active fixation helix tip and wherein the lead connector end includes a contact pin proximally extending from the lead connector end. The tool includes a feature configured to couple to the contact pin and a first mechanism configured to convert linear movement into rotational movement of the contact pin relative to the lead connector end. The tool may further include a second mechanism that causes a stylet extending through the tool and into the contact pin to at least one of distally and proximally displace within the contact pin.

In another embodiment, the tool includes: a feature configured to couple to the contact pin; and a means for converting linear movement into rotational movement of the contact pin relative to the lead connector end. The tool may further include a means for causing a stylet extending through the tool and into the contact pin to at least one of distally and proximally displace within the contact pin.

In yet another embodiment, the tool may include a handle, a worm gear, an axle and a first feature. The handle may include a first digit engagable member linearly displaceable along the handle. The worm gear may be operably coupled to the handle and the first digit engagable member, wherein linear displacement of the first digit engagable member may result in rotational displacement of the worm gear. The axle may be operably coupled to the worm gear and configured to operably couple with the contact pin, wherein rotation of the worm gear results in rotation of the axle. The first feature may engage the lead connector end, wherein rotation of the axle causes the contact pin to rotate relative to the lead connector end. The tool may further include a second digit engagable member linearly displaceable along the handle and operably coupled to a second feature configured to engage a stylet extending through the handle and into the contact pin.

In yet another embodiment, the tool is for implanting a cardiac electrotherapy lead including an active fixation helix tip and a lead connector end including a contact pin. In one embodiment, the tool includes a handle and a rotation mechanism. The handle may include a first member displaceable relative to the handle. The rotation mechanism may include a contact pin engagement feature rotatable relative to the handle and operably coupled to the first member. Displacement of the first member causes the contact pin engagement feature to rotate. In one embodiment, the tool may further include a second member displaceable relative to the handle. Displacement of the second member causes a stylet to at least one of distally and proximally displace through the contact pin.

Also disclosed herein is method of implanting a cardiac electrotherapy lead including an active fixation helix tip and a lead connector end including a contact pin mechanically coupled to the helix tip, wherein rotation of the contact pin causes rotation of the helix tip. In one embodiment, the method includes: providing the lead and a delivery tool; coupling the lead connector end to the tool, wherein the contact pin is operably coupled to a rotation mechanism of the tool; and linearly displacing a first member on a handle of the tool, the linear displacement causing the rotation mechanism of the tool to rotate the contact pin relative to the lead connector end.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3 is a plan view of a bipolar implantable lead having an active fixation distal tip.

FIG. 4 is an isometric view of the lead distal end with the helix tip retracted within the lead distal end.

FIG. 5 is a distal isometric view of the tool with a lead having a lead connector end ready for being received in an opening in the distal end of the tool.

FIG. 6 is a proximal isometric view of the tool with a sheath and a stylet therein received in an opening in the proximal end of the tool.

DETAILED DESCRIPTION

Figure 1:
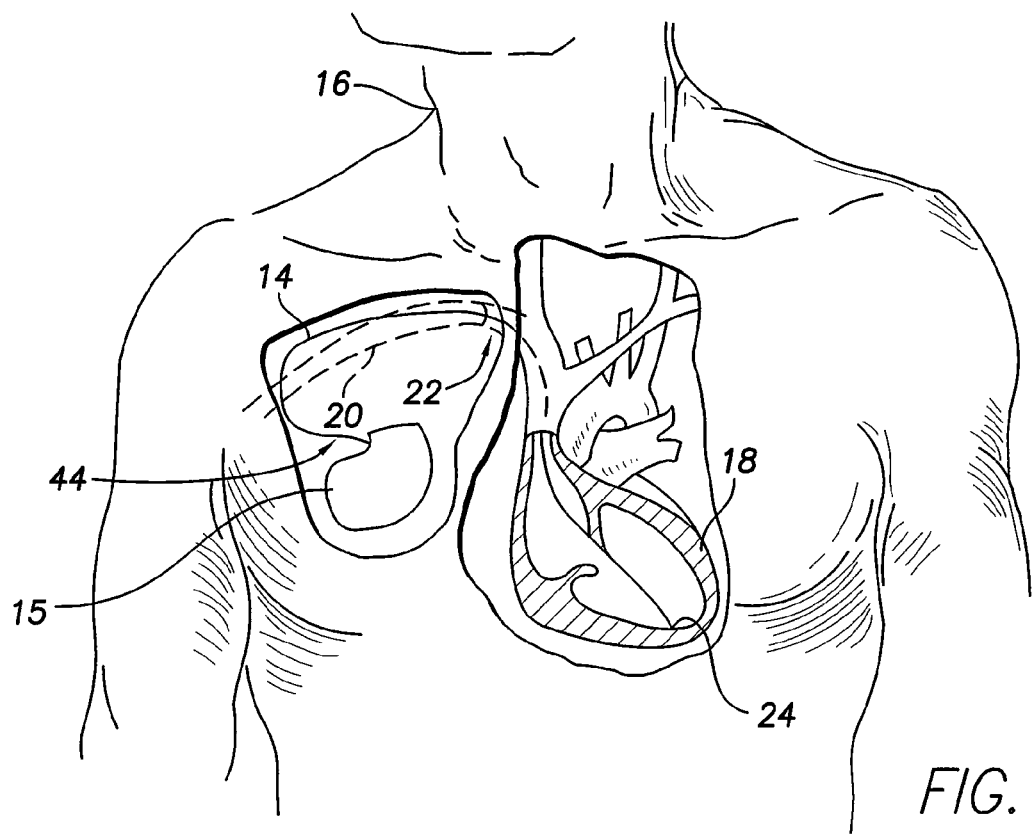
FIG. 1 shows a portion of a patient chest region opened up to illustrate a common technique for transvenously implanting an endocardial lead and subcutaneously implanting a pulse generator mechanically and electrically coupled to a proximal end of the lead.

A tool 50 for assisting in the implantation of an implantable medical lead 14 is disclosed herein. In one embodiment the tool 50 is configured to cause a helix tip 30 to extend from a lead distal tip 24 and retract into the lead distal tip 24. The tool 50 includes a frame 52, a saddle 54 and a mechanism 84 that converts linear displacement of the saddle 54 into rotational displacement of a contact pin 46 of a lead connector end 44 received in a distal end 60 of the tool 50. Thus, linear displacement of the saddle 54 may cause rotational displacement of the helix tip 30 relative to the rest of the lead distal end 24. Depending on the direction of the linear displacement and the resulting rotational displacement of the helix tip 30, the helix tip 30 may extend from the lead distal end 24 for fixation of the lead distal end to cardiac tissue or retract into the lead distal end for removing the helix tip from cardiac tissue.

The mechanism 84 may be configured to result in a predetermined number of rotations of the helix tip 30 for a displacement of the saddle 54 over its full range of motion. Thus, the likelihood of the helix tip 30 being over rotated so as to penetrate the heart wall or damage the lead is substantially reduced. Also, the likelihood of the helix tip 30 achieving inadequate fixation is also substantially reduced. Finally, the physician need not count the number of rotations, but simply fully displace the saddle 54 along its full range of motion to achieve the ideal number of rotations for the helix tip 30.

In one embodiment, the tool 50 further includes a mechanism 86 that linearly displaces a stylet 82 extending through the tool 50 and into the contact pin 46. Thus, the tool 50 may allow for the locating of the lead distal end 24 at the lead implantation site followed immediately by the rotation of the helix tip 30 to achieve fixation of the lead distal end 24 at the lead implantation site. Accordingly, the tool 50 reduces the overall number of tools needed for the implantation of a lead 14 and reduces the time and complexity associated with the implantation of a lead.

The description provided herein is of the best mode presently contemplated for manufacturing and using the tool 50. This description is not to be taken in a limiting sense, but is made merely for the purpose of describing the general principles of the tool 50 and its methods of manufacture and use. The scope of the tool 50, its use and manufacture should be determined with reference to the claims.

Before describing the tool 50 in detail, it will first be helpful to briefly review the manner in which an implantable lead 14 is normally implanted within a patient. Such review will not only help point out the advantages of using a lead having an extendable/retractable positive fixation tip, but will also help highlight the need for the tool 50.

Reference is thus made to FIG. 1 where there is shown a common technique for transvenously implanting an endocardial lead 14 within the heart 18 of a patient 16. A subclavian vein 20 is entered at a desired puncture point 22. The lead 14 is inserted through the puncture point until a distal tip 24 of the lead is at a desired tissue contact location within the heart. While this tissue contact location is shown as being near the apex of the ventricle in FIG. 1, it is to be understood that this is only exemplary and that there are numerous possible tissue contact locations within the heart, both within the ventricle and the atrium.

The proximal end 44 of the lead 14 is then routed to a desired location for connection with an implantable pulse generator 15, e.g., a pacemaker or implantable cardioverter defibrillator ("ICD"), implanted subcutaneously within the patient. Conventional implantation techniques well known in the art are used in implanting the lead 14 and its implantable pulse generator.

Where the lead 14 includes a positive fixation distal tip, which is assumed for purposes of the tool 50, it is thus evident from FIG. 1 and implantation methods well known in the art that the positive fixation tip not protrude from the lead distal end 24 until such time as the distal tip has been positioned at the desired tissue contact location. Otherwise, the tip could easily snag on the vein wall, or a non-desired tissue location in the heart, thereby causing undesirable tissue damage and/or trauma for the patient.

Figure 2:
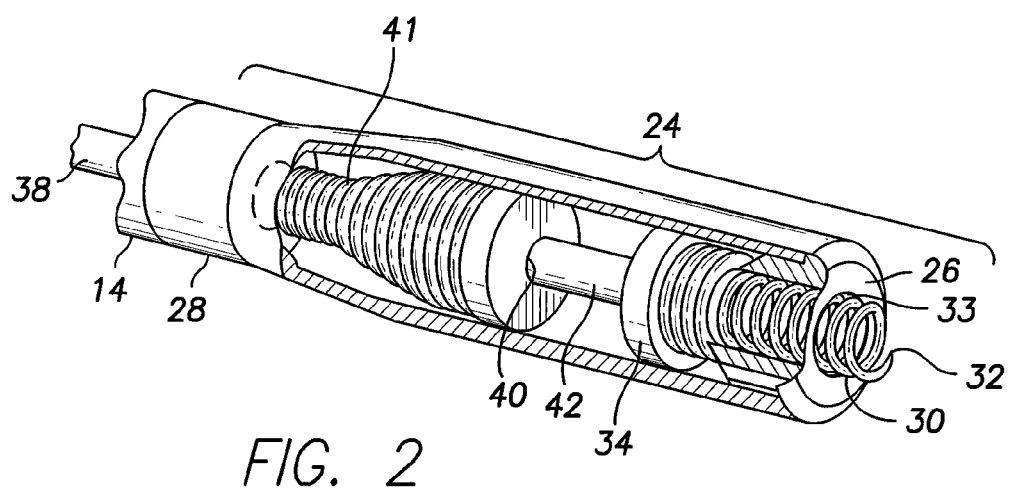
FIG. 2 is an end view, partially broken away, of a bipolar implantable lead having an active fixation distal tip, showing the active fixation tip in its extended position.

Referring next to FIG. 2, an enlarged view of the distal end 24 of an implantable lead 14 having an extendable/retractable positive fixation tip is illustrated. The extendable/retractable fixation tip in FIG. 2 is shown in its extended position. Portions of the distal end shown in FIG. 2 are cut away for clarity. It is noted that the lead shown in FIG. 2 is a bipolar lead, including both a tip electrode 26 and a ring electrode 28. However, it is to be understood that the 50 is not limited to use with a bipolar lead, as any lead having an extendable/retractable positive fixation tip and that is located by a stylet could be used with the invention.

The distal end 24 of the lead 14 shown in FIG. 2 includes a screw-in tip 30 as the positive fixation means. This screw-in tip may include a wire wound in the shape of a helix, ending in a sharp point 32. When extended, as shown in FIG. 2, the screw-in helix tip 30 protrudes out from a hole or opening 33 in the center of the tip electrode 26. When retracted, as shown in FIG. 4, which is an isometric view of the lead distal end 24, the entire screw-in tip 30 is pulled back inside of the opening 33. In some embodiments, the helix tip 30 may also serve as an electrode.

A proximal end of the screw-in tip 30 is secured to a carrier member 34, and the carrier member and screw-in tip may axially displace within the distal end 24 when caused to rotate relative to the distal end 24. A distal end 40 of the inner coil 41 is coupled to a proximal end 42 of the carrier member 34. The inner coil 41, carrier member 34 and helix tip 30 are rotatable within the lead body about a longitudinal axis of the lead body. Thus, rotation of the inner coil 41 in a first direction causes the carrier member and helix tip to rotate and axially extend out of the lead distal end 24 through the opening 33 in distal end 24 for fixation to heart tissue. Rotation of the inner coil 41 in a second opposite direction causes the carrier member and helix tip to rotate and axially retract into the lead distal end 24 through the opening in the distal end 24 to disengage from heart tissue.

The inner coil 41 may define a central lumen of the lead 14. A stylet wire 38 may be inserted through the central lead lumen to negotiate the lead distal end 24 through the vasculature and heart chambers and locate the lead distal end at the implantation site where the lead distal end will be affixed to the heart tissue via the helix tip 30.

FIG. 3 shows a plan view of the bipolar implantable lead 14 having an extendable/retractable positive fixation tip 24 in its extended position, a suture sleeve 39 and a lead connector end 44 at a proximal end 47 of the lead 14. The suture sleeve 39 may include two eyelets 43, slidably passes over the body of the lead 14, and provides a convenient feature for the implanting physician to anchor the lead body within the patient after the distal tip has been properly positioned and secured.

The proximal end 47 of the lead 14 may include an IS-1, IS-4, DF-1 or other type of lead connector end 44 for mechanically and electrically coupling to a pulse generator 15. Such lead connector ends are well known in the in the art. The connector end 44 may include a hollow contact pin 46 that is electrically connected to the distal electrode 26 and, alternatively or additionally, to the helix tip 30 via the inner coil 41. A proximal contact ring 48, if used, is electrically connected to the distal ring electrode 28 via another electrically conductive route through the lead body, typically in the form of another coil conductor radially extending about the inner coil 41 or in the form of a cable conductor routed longitudinally through the wall material forming the lead body.

The lead connector end 44 may include other contact rings that are electrically coupled to other ring electrodes near the lead distal end 24 or defibrillation coils proximal of the lead distal end 24. The lead connector end 44 may also include seals 49. When the lead connector end 44 is received in the pulse generator 15 to mechanically and electrically couple the lead connector end 44 to the pulse generator 15, the contact pin 46 and one or more ring contacts 48 electrically couple to the electrical components of the pulse generator. Also, the seals 49 create a seal between the lead connector end 44 and the pulse generator 15 to prevent body fluids from encountering the contacts 46, 48 or the electrical components of the pulse generator.

The contact pin 46 may be hollow to provide access for a stylet to enter into extend along the central lumen defined by the inner coil 41. The contact pin 46 may be rotatable relative to the rest of the lead connector end 44 and, since the contact pin 46 is mechanically coupled to the inner coil 41, which is mechanically coupled to the helix tip 30, rotation of the contact pin 46 relative to the connector end 44 may be used to cause the helix tip 30 to rotate out of the lead distal end opening 33 or into the lead distal end opening 33, depending on the direction of the rotation of the contact pin 46.

For a detailed discussion of the tool 50, reference is made to FIGS. 5 and 6, which are respectively front and rear isometric views of the tool 50. As shown in FIGS. 5 and 6, the tool 50 may include a hand graspable frame, handle or housing 52, a helix tip saddle 54, and a pair of stylet saddles 56', 56". The housing 52, which may be an ergonomically formed handle, may include a proximal end 58, a distal end 60, a top surface 62, a bottom surface 64, a left side 66, and a right side 68. The top surface 62 may include a longitudinally extending slot 70 along which the helix saddle 54 extends distally-proximally. Similarly, each side surface 66, 68 may include a longitudinally extending slot 72', 72" along which the respective stylet saddle 56', 56" extends distally-proximally. The distal end 60 includes a window 74 and an opening 76 in which the lead distal end 44 is received when the tool 50 is utilized in the implantation of the lead 14. The window 74 allows the contact pin 46 to be viewed when the lead connector end 44 is received the housing distal end 60. The proximal end 58 includes an opening 78 that receives a sheath 80 through which the stylet 82 extends into the tool 50 and the central lumen of the lead 14 when the lead connector end 44 is received in the distal hole 76.

Figure 7:
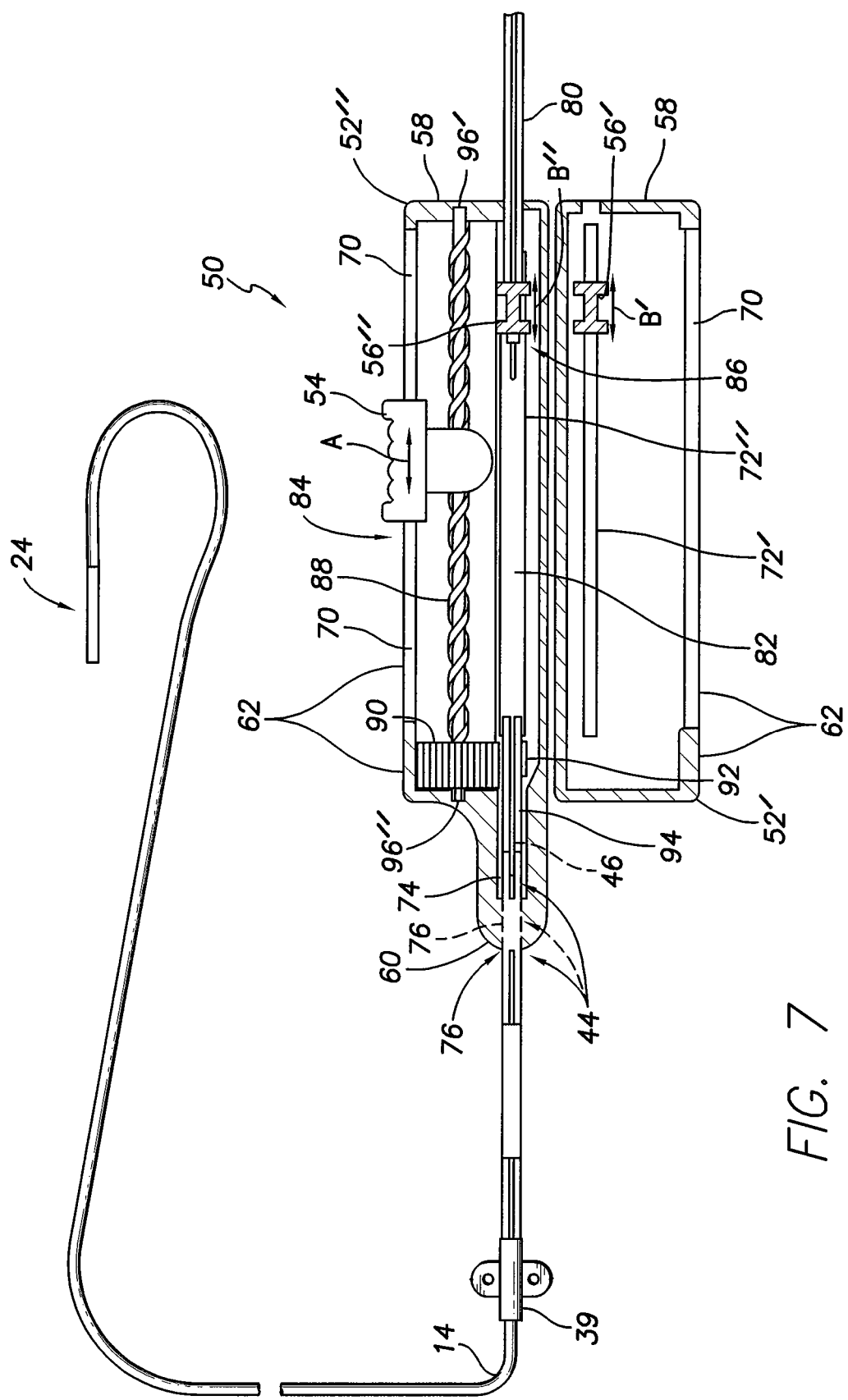
FIG. 7 is a side view of the tool coupled to a lead connector end with the housing opened up into left and right halves to reveal the mechanism therein.

As shown in FIG. 7, which is a side view of the tool 50 coupled to a lead connector end 44 with the housing 52 opened up into left and right halves 52', 52" to reveal the mechanisms 84, 86 therein, the helix tip mechanism 84 may include the saddle 54, a worm gear 88, a large diameter toothed gear 90, a small diameter toothed gear 92, and a pin engagement feature 94 that receives the contact pin 46 when the lead connector end 44 is received in the distal opening 76 of the housing 52. The worm gear 88 extends through the saddle 54 and rotatably mounted in the housing 52 via proximal and distal axle points 96', 96". The large diameter toothed gear 90 is mounted on the distal end of the worm gear 88 such that the worm gear 88 and large diameter toothed gear 90 share a common rotational axis, which is the longitudinal rotational axis of the worm gear 88.

The pin engagement feature 94 may be the axle 94 of the small diameter gear 92 and be in the form of a cylinder or hollow pin 94 in which the contact pin 46 may be received. The pin engagement feature 94 may be rotatably mounted in the housing 52 near the distal end 60 such that the rotational axis of the pin engagement feature 94 is generally is offset and parallel to the rotational axis of the worm gear 88. The small diameter toothed gear 92 extends about the pin engagement feature 94 such that the rotational axis of the pin engagement feature 94 is also the rotational axis of the small diameter toothed gear 92. The teeth of the small diameter toothed gear 92 are in meshed engagement with the teeth of the large diameter toothed gear 92.

As indicated by arrow A, the saddle 54 may proximally-distally displace along the slot 70 and, in doing so, may cause the worm gear 88, with which the saddle 54 is in a mechanical or gear-type engagement, to rotate about its end axles 96', 96". Thus, the saddle 54, which may be engaged by the thumb or other digit of the physician, may be displaced longitudinally along the slot 70 of the housing 52 and, in doing so, cause the worm gear 88 to rotate about its longitudinal axis. The worm gear 88 rotating causes the large diameter toothed gear 90 to rotate, which, in turn, causes the small diameter toothed gear 92 to rotate. The rotating of the small diameter toothed gear 92 causes the pin engagement feature 94 to rotate. The pin engagement feature 94 receives the contact pin 46 in a friction fit, interference fit or setscrew arrangement such that there is no displacement between the feature 94 and the contact pin 46. Similarly, the distal end hole 76 receives the lead connector end 44 in a friction fit, interference fit or set screw arrangement such that there is no displacement between the connector end 44 and the hole 76. Accordingly, when the pin engagement feature 94 is caused to rotate and the lead connector end 44 is prevented from rotating, the contact pin 46 is caused to rotate relative to the lead connector end 44, thereby causing the helix tip 30 to rotate into or out of the lead distal end 24 as can be understood from the discussion provided above with respect to FIGS. 1-4.

In one embodiment, as can be understood from arrow A in FIGS. 5-7, when the saddle 54 is distally displaced, the distal linear movement will be converted via the mechanism 84 into rotational movement of the helix tip 30 that will cause the helix tip to extend out of the distil tip opening 33 and screw into cardiac tissue. Conversely, when the saddle 54 is proximally displaced, the proximal linear movement will be converted via the mechanism 84 into rotational movement of the helix tip 30 that will cause the helix tip to retract into the distil tip opening 33 and unscrew from cardiac tissue.

As illustrated in FIGS. 5-7, in one embodiment, the tool 50 may include a stylet actuation mechanism 86. Each housing portion 52', 52" may include a longitudinally extending slot 72', 72" along which the saddles 56', 56" may distally-proximally displace. The saddles 56', 56" may be coupled together such that displacement of one saddle 56', 56" causes the other saddle 56', 56" to displace in an identical manner. The saddle 56 may include an opening or feature through which a stylet 82 may extend in a fixedly engaged fashion with the saddle 56. Thus, the slots 72', 72", saddles 56', 56" and stylet engagement aspect of the saddles may act together as the mechanism 86.

As indicated in FIG. 7, in one embodiment, the stylet 82 may be preloaded into the sheath 80, through the saddle 56 and housing 52 and into the central lumen of the lead 14 via the contact pin 46 once the lead connector end 44 is received in the tool distal end 60. The stylet 82 may be grasped via the saddle 56 via a friction fit, interference fit or setscrew arrangement such that the stylet will distally-proximally displace when the saddle 56 is distally-proximally displaced along the longitudinally extending slots 72', 72". Thus, as indicated by arrows B', B" of FIGS. 5-7, either of the saddles 56', 56", which may be engaged by the thumb or other digit of the physician, may be displaced longitudinally along the slots 72', 72" of the housing 52 and, in doing so, cause the stylet 82 to distally-proximally displace within the lead central lumen. In one embodiment, distal displacement of a saddle 56', 56" may cause the stylet 82 to distally displace within the lead central lumen, and proximal displacement of the saddle 56', 56" may cause the stylet 82 to proximally displace within the lead central lumen.

In use, the saddle 56 may be used to extend and retract the stylet within the lead 14 as needed to negotiate the lead distal end 24 through the vasculature and heart chambers of the patient and to locate the lead distal end 24 at the implantation site. Once the lead distal end 24 is located at the implantation site via operation of the stylet 82 made possible by the stylet actuation mechanism 86, the helix actuation mechanism 84 may be employed to immediately cause the helix tip 30 to screw into the cardiac tissue of the lead implantation site. As a result, the tool 50 reduces the number of devices need for the lead implantation, reduces the likelihood the lead distal end 24 will migrate before the helix tip 30 can be screwed into the cardiac tissue, and reduces the time and complexity of the procedure.

In one embodiment, the helix actuation mechanism 84 is configured such that displacement of the saddle 54 along the full length of the slot 70 may cause the helix tip 30 to rotate a fixed predetermined number of rotations, e.g., between approximately 10 full rotations of the helix tip 30 and approximately 20 full rotations of the helix tip 30. Such number of full rotations of the helix tip 30 may be based on a preferred number of rotations that is most likely to result in proper fixation with a minimum chance of lead damage or cardiac wall penetration by the helix tip 30. Such predictable number of rotations via a full displacement of the saddle 84 will free the physician from having to count the number of rotations and increase the likelihood of a good outcome.

In one embodiment, the housing 52 is formed of polymer materials such as, for example, acrylonitrile butadiene styrene ("ABS") or etc. or from metal materials, such as, for example, stainless steel, aluminum or etc. The saddles 54, 56 may be formed of polymer materials such as, for example, ABS or etc. or from metal materials, such as, for example, stainless steel, aluminum or etc. Finally, the gears 88, 90, 92 and the pin receiving feature 94 may be formed of polymer materials such as, for example, ABS or etc. or from metal materials, such as, for example, stainless steel, aluminum or etc.

Although the present invention has been described with reference to preferred embodiments, persons skilled in the art will recognize that changes may be made in form and detail without departing from the spirit and scope of the invention.

What is claimed is:

1. A method of implanting a cardiac electrotherapy lead having an active fixation helix tip and a lead connector end having a contact pin mechanically coupled to the helix tip, wherein rotation of the contact pin causes rotation of the helix tip, the method comprising:
   providing the lead and a delivery tool;
   linearly displacing a first digit engagable member of the tool along a handle of the tool, wherein linear displacement of the first digit engagable member results in rotational displacement of a worm gear of the tool, and wherein the worm gear is operably coupled to the handle and the first digit engagable member;
   rotating an axle of the tool, wherein rotation of the worm gear results in rotation of the axle, wherein the axle is operably coupled to the worm gear and is configured to operably couple with the contact pin, and wherein the axle has a first toothed gear and the worm gear has a second toothed gear in toothed engagement with the first toothed gear; and
   engaging a feature of the tool to the lead connector end, wherein rotation of the axle causes the contact pin to rotate relative to the lead connector end.

2. The method of claim 1, wherein the diameter of the second toothed gear exceeds the diameter of the first toothed gear.

3. The method of claim 1, wherein the linear displacement of the first digit causes the helix tip to screw into cardiac tissue at the implantation site.

4. The method of claim 1, wherein the displacement of the first digit relative to the handle is linear.

5. The method of claim 1, wherein the linear displacement is in a distal-proximal direction.

\* \* \* \* \*